United States Patent [19]

Shen

[11] Patent Number: 5,124,498
[45] Date of Patent: Jun. 23, 1992

[54] SYNTHESIS OF OLEFINS FROM CARBONYLS

[75] Inventor: Dong M. Shen, Lawrenceville, N.J.

[73] Assignee: Mobil Oil Corporation, Fairfax, Va.

[21] Appl. No.: 598,499

[22] Filed: Oct. 16, 1990

[51] Int. Cl.$^5$ .............................................. C07C 1/207
[52] U.S. Cl. ..................................... 585/606; 423/499
[58] Field of Search .................. 423/499; 585/603, 606

[56] References Cited

U.S. PATENT DOCUMENTS

| | | | |
|---|---|---|---|
| 2,765,270 | 10/1956 | Brenner et al. | 423/463 |
| 2,856,335 | 10/1958 | Rick | 423/499 |
| 4,225,734 | 9/1980 | McMurry | 585/409 |

OTHER PUBLICATIONS

41 J. Org. Chem. 896 (1976).
43 J. Org. Chem. 3255 (1978).
60 Org. Synthesis 113 (1981).

Primary Examiner—Wayne Langel
Attorney, Agent, or Firm—Alexander J. McKillop; Charles J. Speciale; Robert B. Furr, Jr.

[57] ABSTRACT

The invention provides, in a first aspect, a method for preparing a reduced metal reagent comprising the steps of providing a halide salt of a metal having a more positive reduction potential than Na in admixture with liquid Na in substantially stoichiometric quantities in the presence of an ogranic solvent characterized by boiling point, measured at atmospheric conditions, at least equal to the melting point of Na, to reduce substantially all of the halide salt to reactive metal reagent and to convert substantially all of said Na to a Na halide salt.

The invention further provides, in a second aspect, a method for converting carbonylsin the presnece of the reduced metal reagent prepared in accordance with the invention.

18 Claims, No Drawings

SYNTHESIS OF OLEFINS FROM CARBONYLS

FIELD OF THE INVENTION

The present invention relates to the field of reactive metal reagents. More specifically, the invention relates to a method for preparing a reactive metal reagent from a halide salt of the metal, and further includes a method for converting a carbonyl, i.e., an aldehyde or ketone, in the presence of the reactive metal reagent. The reactive metal reagent is useful for converting carbonyls to olefins, particularly symmetrical olefins. This application is related by subject matter to application Ser. No. 598,498, filed on even date herewith, now U.S. Pat. No. 5,053,434.

BACKGROUND OF THE INVENTION

Reactive metal reagents are generally useful for reducing a variety of organic substrates, for example reducing ketones and aldehydes to olefins. See U.S. Pat. No. 4,225,734 to McMurry, which is incorporated by reference as if set forth at length herein for the details of such conversions. The McMurry '734 patent teaches reducing Ti(III) or Ti(IV) in the form of $TiCl_3$ or $TiCl_4$ to obtain the $Ti°$ active metal reagent. Suitable reducing agents are said to include alkali metals, for example sodium, potassium, or lithium. See the McMurry '734 patent at column 4, lines 21-24. Specific examples include $LiAlH_4$ (Example II), $LiBH_4$ (Example XIII), and K metal (Example XV).

The literature, however, acknowledges certain problems with the use of reduced metal catalysts as disclosed in the McMurry '734 reference. For example, some workers in the field reported difficulty in coupling saturated aliphatic ketones using $Ti°$ which had been reduced in the presence of $LiAlH_4$. Reducing $Ti°$ via Rieke's method (K metal, $TiCl_3$, in tetrahydrofuran (THF) solvent) was subsequently found to reliably convert both aliphatic and aromatic ketones to the corresponding symmetrical olefins. See McMurry, 41 *J. Org. Chem.* 896 (1976).

Further, the effectiveness of a particular combination of carbonyl feedstock and reducing agent has proven to be unpredictable. Low-valent titanium reagents ($TiCl_4/Zn$, $TiCl_3/Mg$, $TiCl_3/LiAlH_4$) have been examined, and the results for the attempted dimerization of various aldehydes and ketones with the $TiCl_3/LiAlH_4$ reagent are unpredictable, and have been described as "capricious". See McMurry, et al., 43 *J. Org. Chem.* 3255 (1978).

Moreover, the McMurry, et al. article notes that both the reaction of Li metal to the halide salt and the reduction of Ti(III) to $Ti°$ are incomplete, leaving residual reducing agent on the filter cake. See McMurry, et al. at page 3255, column 2, as well as the Experimental Section at page 3263 et seq. Particularly, the reference notes that the filter cake resulting from $TiCl_3$ reduction with K metal is pyrophoric. Thus removing the reactive residual metal-containing reagents from the product mixture, particularly by means such as aqueous acid workup, has proven to be a major obstacle in purifying carbonyl reduction products. For example, in some cases, washing with acid, for example, cold 2N aqueous HCl, is the only practical and effective means for removing residual Li metal from the olefin product. Clearly, it would be desirable to avoid the potentially hazardous procedure of contacting a reactive metal with an aqueous acid.

The McMurry et al. article further notes that excess $TiCl_3$ as well as excess reducing agent, i.e., $LiAlH_4$, is required due to the characteristically incomplete reaction of the Ti halide salt and the reducing agent. Thus it would further be desirable to decrease reagent costs for carbonyl coupling reactions by employing substantially stoichiometric quantities of the metal compound and the reducing agent.

SUMMARY OF THE INVENTION

The method of the present invention overcomes many of the disadvantages of previously known methods for generating reduced metal reagents for organic synthesis reactions. The halide salt of the reactive catalytic metal as well as the reducing agent may suitably be used in near-stoichiometric quantities. Further, the invention substantially eliminates the need for removing reactive metal-containing residual from the olefin product. Small amounts of $Ti°$ may be present in the crude olefin product, but removing this residual $Ti°$ is notably simpler and less dangerous than removing residual Li or K.

The invention provides, in a first aspect, a method for preparing a reactive metal reagent comprising the steps of providing a halide salt of a metal having a more positive reduction potential than Na in admixture with liquid Na in substantially stoichiometric quantities in the presence of an organic solvent characterized by boiling point, measured at atmospheric conditions, at least equal to the melting point of Na, to reduce substantially all of said metal and to convert substantially all of said Na to a Na halide salt.

The method provides, in a second aspect, a liquid phase method for converting an aldehyde or a ketone to a symmetrical olefin in the presence of a reduced metal catalyst comprising the steps of:

(a) providing a halide salt of a metal having a more positive reduction potential than Na;

(b) admixing liquid Na with a liquid organic solvent having a boiling point of at least the melting point of Na under temperature conditions sufficient to maintain Na in the liquid state;

(c) reducing said metal of step (a) in the presence of said liquid Na and said organic solvent of step (b);

(d) reacting an aldehyde or ketone in solution with the organic solvent of step (c).

DETAILED DESCRIPTION

In accordance with the present inventive method, the metal halide reagent and the reducing metal, sodium, are reacted substantially to extinction thus eliminating the necessity of removing the unreacted reactive metal and metal salts from the product mixture. The method finds utility in numerous reactive metal-induced organic synthesis reactions in addition to carbonyl coupling, examples of which include converting unreactive organohalides to Grignard reagents using $Mg°$, and reacting $Zn°$ with alpha-bromoesters to produce organozinc reagents for reactions with carbonyl compounds in the Reformatsky reaction.

Feedstocks useful in the carbonyl coupling synthesis of the present invention include both aliphatic and aromatic, cyclic and acyclic, saturated and unsaturated aldehydes and ketones, nonlimiting examples of which include n-heptanal, acetone, acetophenone, benzophenone, benzaldehyde, cinnamaldehyde, cyclohexanone, and adamantanone.

In contrast to many previously known metal-induced carbonyl coupling reactions, the present method is effective both for aromatic as well as for aliphatic carbonyls.

Any metal halide having a more positive reduction potential than that of Na may be effectively used in accordance with the present invention. Nonlimiting examples of metal halides useful for reduction in accordance with the present invention include $TiCl_3$, $TiCl_4$, $VCl_3$, $MgBr_2$, $MgCl_2$, $ZnCl_2$, $ZnBr_2$, $NiCl_2$, $NiBr_2$, $FeCl_3$, and $FeBr_3$. Preferred metal halides include $TiCl_3$, $TiCl_4$, and $VCl_3$.

The organic solvent of the invention must boil at or above the melting point of Na metal. Examples of such solvents include 1,4-dioxane (b.p. 101.3° C.) as well as n-butyl ether (b.p. 142.2° C.), diglyme (b.p. 162.0° C.), and triglyme (b.p. 216.0° C.), merely to name a few. The reduction and the subsequent reaction of the present invention are not necessarily carried out at the boiling point of the solvent used, but the reduction must be conducted at a temperature sufficient to maintain the sodium metal in the liquid state.

EXAMPLES

The following Examples were conducted with the following general experimental procedure.

Titanium trichloride is refluxed with small (about 5 mm on a side) blocks of sodium in dry 1,4-dioxane under an Ar atmosphere with stirring for about 1-2 hours, or until no sodium particles can be seen and a black slurry is formed. The carbonyl compound is then added, typically in one portion from the top of the condenser. The mixture is then refluxed for about another 15 hrs. to complete the reaction. A suitable solvent, or mixture of solvents such as hexanes are added to the flask after cooling, and the black mixture is filtered through a pad of silica gel or Florisil. The Florisil was washed with an additional quantity of solvent such as hexanes. The product is then purified by recrystallization, distillation, or both.

EXAMPLE 1

One (1) part of adamantanone was treated with 4 parts of $TiCl_3$ and 12 parts Na in 1,2-dimethoxyethane (DME) solvent (b.p. 85° C.) in accordance with the following procedure.

Titanium trichloride (6.170 grams, 40.0 mmol) was weighed into a 3-necked flask in an argon glove bag. The flask was cooled over ice, and 60 ml of dry DME was added with stirring. Chunks of sodium metal (about 5 mm on a side) were then added (2.759 grams, 120.0 mmol). The mixture was heated to reflux with stirring under an argon blanket. The adamantanone (1.502 grams, 10.0 mmol) was added to the refluxing mixture. The reactant mixture was maintained under reflux for 32 hours. The product mixture was filtered with hexanes over a silica gel pad, dried and the solvents were removed by evaporation. The sodium chunks were recovered and weighed (2.3 grams). NMR analysis of the product mixture revealed a molar product distribution of 21% adamantanone, 3% 2-adamantanol, and 57% adamantylideneadamantane (adamantane dimer).

EXAMPLE 2

The procedure of Example 1 was repeated with less excess $TiCl_3$ and lithium metal instead of sodium. Specifically, 1 part of adamantanone was treated with 1.5 parts of $TiCl_3$ and 4.5 parts Li. Example 2 is conducted in a manner similar to that disclosed in Fleming et al., 60 Org. Synthesis 113 (1981) which employed adamantanone:$TiCl_3$:Li in molar ratios of 1:4:12 to give the dimer olefin adamantylideneadamantane in yields of 84-87%. Example 2 repeats the procedure of the Fleming et al. reference with less excess $TiCl_3$ and Li (adamantanone:$TiCl_3$:Li molar ratios of 1:1.5:4.5) to illustrate the limitations of this previously known method of preparing the reactive metal reagent.

Titanium trichloride (2.314 grams, 15.0 mmol) was weighed into a 3-necked flask in an argon glove bag. The flask was cooled over ice, and 60 ml of dry DME was added with stirring. Small slices of Li wire were added (0.312 grams, 45.0 mmol). The mixture refluxed with stirring under an argon blanket for 7 hours. The adamantanone (1.502 grams, 10.0 mmol) was added to the mixture and reflux was continued for 20 additional hours. The product mixture was purified as described above in Example 1. NMR analysis of the recovered product revealed a yield distribution of 28% adamantanone, 14% 2-adamantanol, and 46% of the dimer olefin adamantylideneadamantane.

EXAMPLE 3

The procedure of Example 2 was repeated using Na metal rather than Li as the reducing agent and 1,4-dioxane (b.p. 101.3° C.) solvent rather than DME.

One (1) part of adamantanone was treated with 1.5 parts of $TiCl_3$ and 4.5 parts Na. Titanium trichloride (2.314 grams, 15.0 mmol) was weighed into a 3-necked flask in an argon glove bag. The flask was cooled over ice, and 25 ml of dry 1,4-dioxane was added with stirring. Small (about 5 mm) chunks of Na metal were added (1.035 grams, 45.0 mmol). The mixture refluxed with stirring under an argon blanket for 45 minutes. No sodium particles were visible. The adamantanone (1.502 grams, 10.0 mmol) was added to the mixture and reflux was continued for 23 additional hours. After cooling, 50 ml of hexanes was added. The product mixture was filtered through Florisil and the filter cake was washed with additional hexanes. NMR analysis of the recovered product revealed essentially pure dimer, with neither unreacted ketone nor byproduct alcohol detected. The dimer, olefin, adamantylideneadamantane was produced in 97% yield.

EXAMPLE 4

One (1.0) part of adamantanone was treated with 1.1 parts of $TiCl_3$ and 3.3 parts Na. Titanium trichloride (1.697 grams, 11.0 mmol) was weighed into a 3-necked flask in an argon glove bag. The flask was cooled over ice, and 20 ml of dry 1,4-dioxane was added with stirring. Small (about 5 mm) chunks of Na metal were added (0.759 grams, 33.0 mmol). The mixture refluxed with stirring under an argon blanket for 30 minutes. A small quantity of finely divided shiny particles could be seen dispersed in the refluxing 1,4-dioxane solvent, which was believed to be attributable to trace impurities in the $TiCl_3$ which reduced the actual amount of $TiCl_3$ available for reaction. The adamantanone (1.502 grams, 10.0 mmol) was added to the mixture and reflux was continued for 23 additional hours, at which no Na was observed. Thus it appeared that the Na reacted with the product of Ti° to convert the product back to Ti°. Workup similar to that of Example 3, above, gave a crude product. The NMR spectrum of this crude product showed only the adamantylideneadamantane product. However, recrystallization of the crude product in 250 ml of methanol gave two crops of pure dimer totalling 1.239 grams, and the third crop of product (45 mg) contained a detectable amount of a byproduct alcohol (2-adamantanol). Adamantylideneadamantane was produced in 95% yield.

EXAMPLE 5

One (1.0) part of adamantanone was treated with 1.0 part of $TiCl_3$ and 3.0 parts Na. Titanium trichloride (30.85 grams, 200 mmol) was weighed into a 3-necked flask in an argon glove bag. The flask was cooled over ice, and about 400 ml of dry 1,4-dioxane was added with stirring. Small (about 5 mm) chunks of Na metal were added (13.80 grams, 600 mmol). The mixture refluxed with stirring under an argon blanket for 2 hours. The adamantanone (30 grams, 200 mmol) was added to the mixture in 5 gram portions over a period of about 15 minutes. The mixture was then refluxed for 20 additional hours. Workup as described above for Example 3 gave a product mixture (white solid, 26.31 grams) which was refluxed with 350 ml of methanol for 4 hours. The refluxed mixture was cooled, filtered, washed with additional methanol, and dried, yielding 24.14 grams of colorless crystals (90% yield).

EXAMPLE 6

The ketone coupling process of the invention was further evaluated with diamantanone with 1.18 part $TiCl_3$ and 3.55 parts Na.

One (1.0) part of diamantanone was treated with 1.18 part of $TiCl_3$ and 3.55 parts Na. Titanium trichloride (10.03 grams, 65 mmol) was weighed into a 3-necked flask in an argon glove bag. The flask was cooled over ice, and about 100 ml of dry 1,4-dioxane was added with stirring. Small (about 5 mm) chunks of Na metal were added (4.483 grams, 195.0 mmol). The mixture was refluxed with stirring under an argon blanket for 2 hours. The diamantanone (11.12 grams, 55.0 mmol) was added to the mixture in several portions over a period of about 30 minutes. The mixture was then refluxed for 38 additional hours. The refluxed mixture was cooled, admixed with 150 ml hexanes, and filtered through a Florisil pad. The residue was washed with hexanes and 1,4-dioxane, and the solvents were evaporated to yield 10.21 grams of white solid product. The white solid product was refluxed with 150 ml of methanol for 1.5 hours. The refluxed mixture was cooled, filtered, washed with additional methanol, and dried, yielding 9.747 grams of white powder (Product A). The solvent (methanol) was then removed from the mother liquor, filtered through silica gel and washed with hexanes, and evaporated, yielding 0.436 grams of a yellowish solid product (Product B).

NMR analysis of Product A revealed a molar ratio of anti-:syn- dimers of about 5:4 (95% yield).

Product B was filtered through about 10 grams of silica gel with 50 ml hexanes. The solvent was evaporated, yielding 0.330 grams of a colorless solid (Product C). NMR analysis revealed a detectable quantity of impurities in Product C.

The total yield for diamantanone dimerization was approximately 97%.

EXAMPLE 7

The ketone coupling process of the invention was evaluated for dimerization of n-heptanal with 1.1 parts $TiCl_3$ and 3.3 parts Na.

Titanium trichloride (1.87 grams, 12.0 mmol) was weighed into an oven-dried 50 ml three-necked round-bottom flask in an argon glove bag. The flask was fitted with a reflux condenser having an Ar bubbler and was cooled with an ice-water bath. After 20 ml of dry 1,4-dioxane was added to the flask with cooling and magnetic stirring, the cooling bath was removed. Sodium (0.83 gram, 36.0 mmol) was added to the flask, and the mixture was refluxed for 1 hour with stirring. After adding 1.14 grams (10.0 mmol) of freshly distilled n-heptanal from the top of the condenser in one portion, reflux was continued for another 15.5 hours. The mixture was cooled, and 20 ml hexane was added to the flask. The resulting black slurry was filtered through a pad of Florisil with hexanes. Removal of solvent gave 0.817 grams of colorless oil which was pure as judged by $^1H$ and $^{13}C$ NMR. Integration of the $^{13}C$ spectrum with relaxation delay of 10 seconds gave a trans/cis ratio of 3.0:1.0. Total yield of the trans-/cis-7-tetradecene was 73%.

EXAMPLE 8

The ketone coupling process of the invention was evaluated for dimerization of cyclohexanone with 1.2 parts $TiCl_3$ and 3.3 parts Na. The cyclohexanone under examination was purchased from Aldrich Chemical Company, 1001 West Saint Paul Avenue, Milwaukee, Wis., 53233, under the Aldrich "Gold Label" designation at a stated purity of 99.8% (weight).

Titanium trichloride (1.87 grams, 12.0 mmol) was weighed into an oven-dried 50 ml three-necked round-bottom flask in an argon glove bag. The flask was fitted with a reflux condenser having an Ar bubbler and was cooled with an ice-water bath. After 20 ml of dry 1,4-dioxane was added to the flask with cooling and magnetic stirring, the cooling bath was removed. Sodium (0.76 gram, 33.0 mmol) was added to the flask, and the mixture was refluxed for 1.3 hours with stirring. After adding 0.980 grams (10.0 mmol) of cyclohexanone from the top of the condenser in one portion, reflux was continued for another 12 hours. Workup as described above in Example 3 gave 0.808 grams of a colorless oil, which partially solidified on standing. The mixture was filtered and the solid was washed with methanol and dried, yielding 0.122 grams of crystals having a melting point range of from about 53° to about 55° C. Estimated yield of cyclohexalydenecyclohexane, accounting for mineral oil contamination in the original crude product, was found to be about 50%.

EXAMPLE 9

The ketone coupling process of the invention was evaluated for dimerization of benzophenone with 1.2 parts $TiCl_3$ and 3.3 parts Na.

Titanium trichloride (1.851 grams, 12.0 mmol) was weighed into an oven-dried 50 ml three-necked round-bottom flask in an argon glove bag. The flask was fitted with a reflux condenser having an Ar bubbler and was cooled with an ice-water bath. After 12 ml of dry 1,4-dioxane was added to the flask with cooling and magnetic stirring, the cooling bath was removed. Sodium (0.759 gram, 33.0 mmol) was added to the flask, and the mixture was refluxed for 2 hours with stirring. Benzophenone was added (1.822 grams, 10.0 mmol) from the top of the condenser in one portion and an additional 3 ml of dry 1,4-dioxane was added to wash down the small amount of ketone remaining in the condenser. Reflux was continued for another 19.25 hours. The mixture was cooled, about 20 ml of hexanes was added to the flask, and the mixture was filtered through a pad of Florisil. The solvent was then evaporated, yielding 1.692 grams of a yellowish solid.

The yellowish solid was refluxed in 80 ml of methanol to recrystallize. Most did not dissolve. The methanol solution was cooled and the solid was collected, washed with additional methanol, and dried, yielding 1.313 grams of a solid having a melting point range of from about 217° to about 218° C. $^1$H and $^{13}$C NMR showed the solid to be tetraphenylethylene (79% yield).

The mother liquor gave a yellow solid on removing solvent which contained a complex mixture of products.

The results of Examples 1-9 are summarized in the following Table.

Changes and modifications in the specifically described embodiments can be carried out without departing from the scope of the invention which is intended to be limited only by the scope of the appended claims.

TABLE

|  | Reactant | Molar Ratio of Metal Halide Salt to Reducing Agent | Solvent | Primary Product | Primary Product Yield |
| --- | --- | --- | --- | --- | --- |
| Example 1 | Adamantanone | 4 TiCl$_3$:12 Na | DME | Adamantylidene-adamantane | 57% |
| Example 2 | Adamantanone | 1.5 TiCl$_3$:4.5 Li | DME | Adamantylidene-adamantane | 46% |
| Example 3 | Adamantanone | 1.5 TiCl$_3$:4.5 Na | 1,4-dioxane | Adamantylidene-adamantane | 97% |
| Example 4 | Adamantanone | 1.1 TiCl$_3$:3.3 Na | 1,4-dioxane | Adamantylidene-adamantane | 95% |
| Example 5 | Adamantanone | 1.0 TiCl$_3$:3.0 Na | 1,4-dioxane | Adamtylidene-adamantane | 90% |
| Example 6 | Diamantanone | 1.18 TiCl$_3$:3.55 Na | 1,4-dioxane | c- and t-Diamantylidene-diamantane | 97% |
| Example 7 | n-Heptanal | 1.1 TiCl$_3$:3.3 Na | 1,4-dioxane | trans-/cis-7-tetradecene | 73% |
| Example 8 | Cyclohexanone | 1.2 TiCl$_3$:3.3 Na | 1,4-dioxane | cyclohexalydene-cyclohexane | 50% |
| Example 9 | Benzophenone | 1.2 TiCl$_3$:3.3 Na | 1,4-dioxane | tetraphenylethylene | 79% |

What is claimed is:

1. A method for converting carbonyl compounds to symmetrical olefins in the presence of a reduced metal reagent comprising the steps of:
   (a) providing in approximately stoichiometric quantity a halide salt of a metal having a more positive reduction potential than Na;
   (b) admixing liquid Na with an oxygen-containing organic solvent having a boiling point of at least the melting point of Na;
   (c) reducing said metal of step (a) in the presence of said liquid Na and said oxygen-containing organic solvent of step (b);
   (d) reacting said carbonyl compounds in solution with the oxygen-containing organic solvent of step (c).

2. The method of claim 1 further comprising recovering symmetrical olefins from said oxygen-containing organic solvent of step (d).

3. The method of claim 2 further comprising recovering olefins from said oxygen-containing organic solvent of step (d) in the absence of a step for removing excess reducing agent.

4. The method of claim 2 wherein said carbonyl compounds are selected from the group consisting of aliphatic ketones, aromatic ketones, cyclic ketones, acyclic ketones, saturated ketones, unsaturated unsaturated ketones, aliphatic aldehydes, aromatic aldehydes, cyclic aldehydes, acyclic aldehydes, saturated aldehydes, and unsaturated aldehydes.

5. The method of claim 4 wherein said carbonyl compounds comprise at least one selected from the group consisting of n-heptanal, acetone, acetophenone, benzophenone, benzaldehyde, cinnamaldehyde, cyclohexanone, and adamantanone.

6. A method for converting an aldehyde or a ketone to an olefin in the presence of a reduced metal reagent comprising the steps of:
   (a) providing in approximately stoichiometric quantity a halide salt of a metal having a more positive reduction potential than Na;
   (b) admixing liquid Na with an oxygen-containing organic solvent having a boiling point of at least the melting point of Na;
   (c) reducing said metal of step (a) in the presence of said liquid Na and said oxygen-containing organic solvent of step (b);
   (d) reacting said aldehyde or ketone in solution with the oxygen-containing organic solvent of step (c).

7. The method of claim 6 wherein said metal is selected from the group consisting of Ti, V, Mg, Zn, Ni and Fe.

8. The method of claim 7 wherein said metal is selected from the group consisting of Ti and V.

9. The method of claim 7 wherein said halide salt is selected from the group consisting of TiCl$_3$, TiCl$_4$, VCl$_3$, MgBr$_2$, MgCl$_2$, ZnCl$_2$, ZnBr$_2$, NiCl$_2$, NiBr$_2$, FeCl$_3$, and FeBr$_3$.

10. The method of claim 8 wherein said halide salt is selected from the group consisting of TiCl$_3$, TiCl$_4$, VCl$_3$.

11. The method of claim 6 further comprising recovering olefins from said oxygen-containing organic solvent of step (d).

12. The method of claim 11 further comprising recovering olefins from said oxygen-containing organic solvent of step (d) in the absence of a step for removing excess reducing agent.

13. The method of claim 6 further comprising recovering olefins from said oxygen-containing organic solvent of step (d) in the absence of an aqueous acid contacting step.

14. The method of claim 6 further comprising recovering olefins from said oxygen-containing organic solvent of step (d) in an oxygen-containing atmosphere.

15. The method of claim 6 wherein said metal is selected from the group consisting of Ti, V, Mg, Zn, Ni and Fe.

16. The method of claim 15 wherein said metal is selected from the group consisting of Ti and V.

17. The method of claim 15 wherein said halide salt is selected from the group consisting of $TiCl_3$, $TiCl_4$, $VCl_3$, $MgBr_2$, $MgCl_2$, $ZnCl_2$, $ZnBr_2$, $NiCl_2$, $NiBr_2$, $FeCl_3$, and $FeBr_3$.

18. The method of claim 16 wherein said halide salt is selected from the group consisting of $TiCl_3$, $TiCl_4$, $VCl_3$.

* * * * *